United States Patent [19]

Markowitz et al.

[11] Patent Number: 4,503,858
[45] Date of Patent: Mar. 12, 1985

[54] DEVICE FOR DETERMINING THE PACING MODALITY OF AN ARTIFICIAL CARDIAC PACEMAKER

[75] Inventors: Harold T. Markowitz, Ham Lake; John C. Rueter, Shoreview; Gary J. Syring, Minneapolis, all of Minn.

[73] Assignee: Medtronic, Inc., Minneapolis, Minn.

[21] Appl. No.: 504,699

[22] Filed: Jun. 15, 1983

[51] Int. Cl.³ ............................................. A61N 1/00
[52] U.S. Cl. .............................................. 128/419 PT
[58] Field of Search ......................... 128/419 PT, 697

[56] References Cited

U.S. PATENT DOCUMENTS

| | | | |
|---|---|---|---|
| 3,651,799 | 3/1972 | Daynard | 128/697 |
| 3,780,727 | 12/1973 | King | 128/697 |
| 3,782,367 | 1/1974 | Hochberg et al. | 128/697 |
| 4,236,524 | 12/1980 | Powell et al. | 128/419 PT |
| 4,290,430 | 9/1981 | Bihn et al. | 128/419 PT |

Primary Examiner—William E. Kamm
Attorney, Agent, or Firm—Glenn W. Bowen; John L. Rooney; Joseph F. Breimayer

[57] ABSTRACT

A pacing system analyzer as connected to an implantable cardiac pacer and if an atrial pacing pulse is detected only, the analyzer sends a simulated P-wave to the pacer and determines the response of the simulated P-wave to determine if the pacing mode is AAI, AAT, or AOO. In the event a ventricular output pulse only is detected by the analyzer, a simulated R-wave is sent to the pacer and if the pacer responds either by a triggered ventricular pulse or by not changing its response, the analyzer determines that the pacer is in a VVT or VOO mode. On the other hand, if the pacer is inhibited a subsequent simulated P-wave is sent to it and the response of this P-wave determines whether or not the pacer is in a VVI or VDD mode. In the event that both atrial and ventricular pacing pulses are detected by the analyzer, the simulated R-wave is first sent to the pacer and an unchanged response determines that the pacer is in a DOO mode. On the other hand, if the pacer is inhibited so that ventricular pulses are not produced, then a simulated P-wave is sent to it. The response of the pacer to the simulated P-wave determines whether it is in a DVI or DDD mode.

3 Claims, 2 Drawing Figures

DEVICE FOR DETERMINING THE PACING MODALITY OF AN ARTIFICIAL CARDIAC PACEMAKER

BACKGROUND OF THE INVENTION

Prior pacing system analyzers have been developed which were suitable for limited analysis of implantable cardiac pacemakers with only one or two possible pacing modalities. The most common being devices which were suitable only for use with ventricular and atrial demand pacing pacers. With the advance of physiologic pacers, and the growth of a variety of programmable pacing modes it has become very desirable to have a pacing system analyzer which is capable of operating with any of the commonly used pacing modalities. Often, however, when a pacing system analyzer is connected to a cardiac pacer it is not known what pacing mode the pacemaker is operating in. In order to confirm the operating mode of the pacemaker, a pacing system analyzer should be capable of distinguishing all of the common pacing modalities. The pacing system analyzer of the present invention is capable of determining which of the ten common possible pacing modalities an artificial pacemaker is in and at any given time.

TECHNICAL DESCRIPTION OF THE INVENTION

Figure 1:
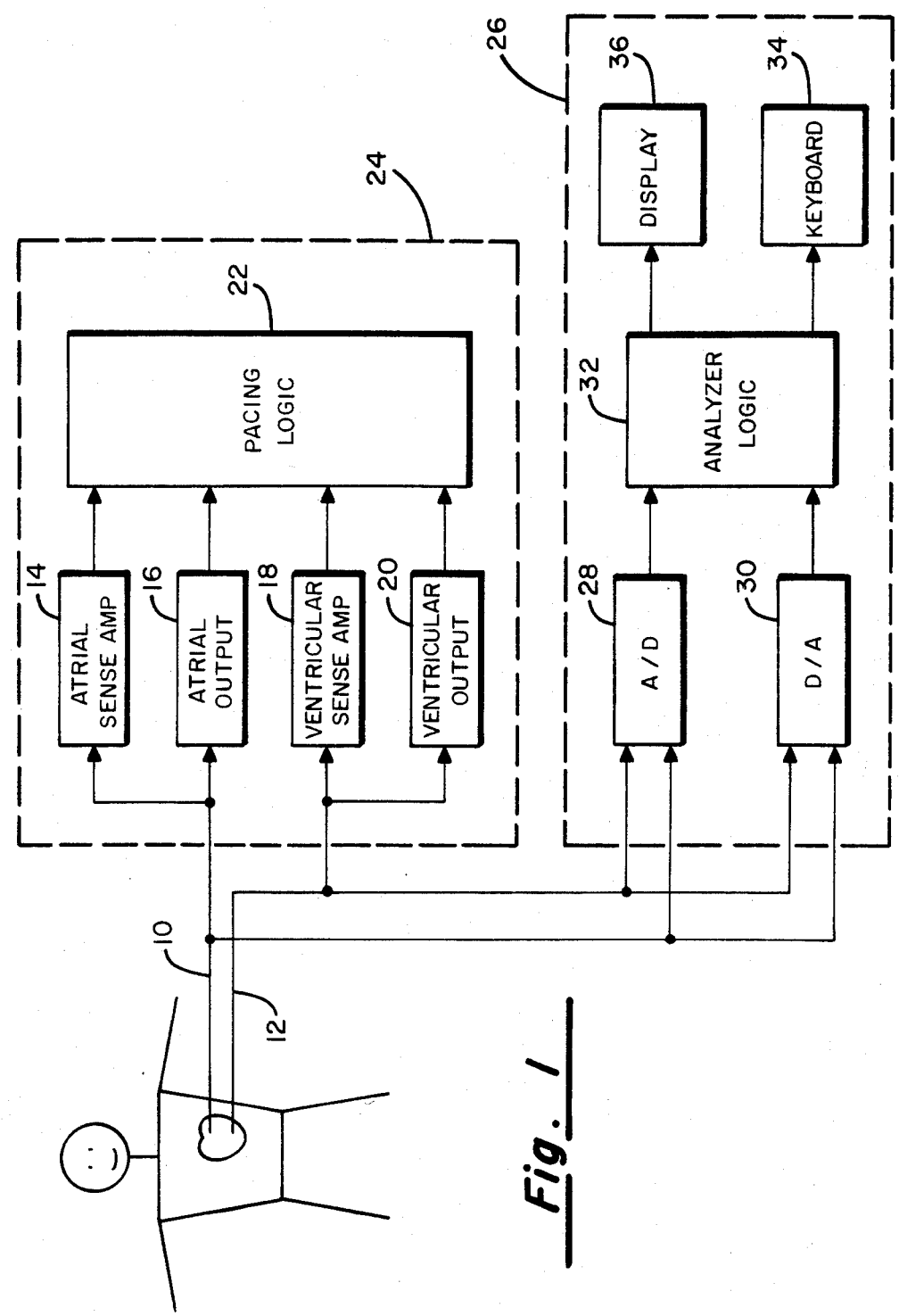
FIG. 1 is a block diagram representation of the overall configuration of the present invention.

The present invention is illustrated by reference to the drawngs in which FIG. 1 shows atrial and ventricular leads that are connected to the heart of a patient. The atrial lead 10 is coupled to an atrial sense amplifier 14 and to an atrial output circuit 16 which supplies pulses to the atrium of the patient through the lead 10, while a sense amplifier 14 senses signals on the lead. A ventricular sense amplifier 18 is coupled to the ventricular lead 12, and a ventricular output circuit 20 is also coupled to the same lead. The pacing logic 22 which controls the circuits 14–20 commonly employs a commercially available microprocessor and with these circuits forms the implantable cardiac pacemaker 24. The leads 10, 12 are coupled to the pacing system analyzer 26, specifically to an analog-to-digital converter 28 and a digital-to-analog converter 30. The analog-to-digital converter 28 is employed to receive analog sensed signals on the leads 10, 12 and to convert these to digital input signals to the analyzer 26. The digital-to-analog converter 30 receives digital signals representative of simulated P and R waves and convertes these to analog P and R simulated waves, which are transmitted to the leads 10 and 12, respectively.

The converters 28, 30 are coupled to the analyzer logic 32 of the analyzer 26, that controls the operation of the analyzer input information is fed to the analyzer logic by the keyboard 34 and output information may be displayed or printed at the display 36.

Figure 2:
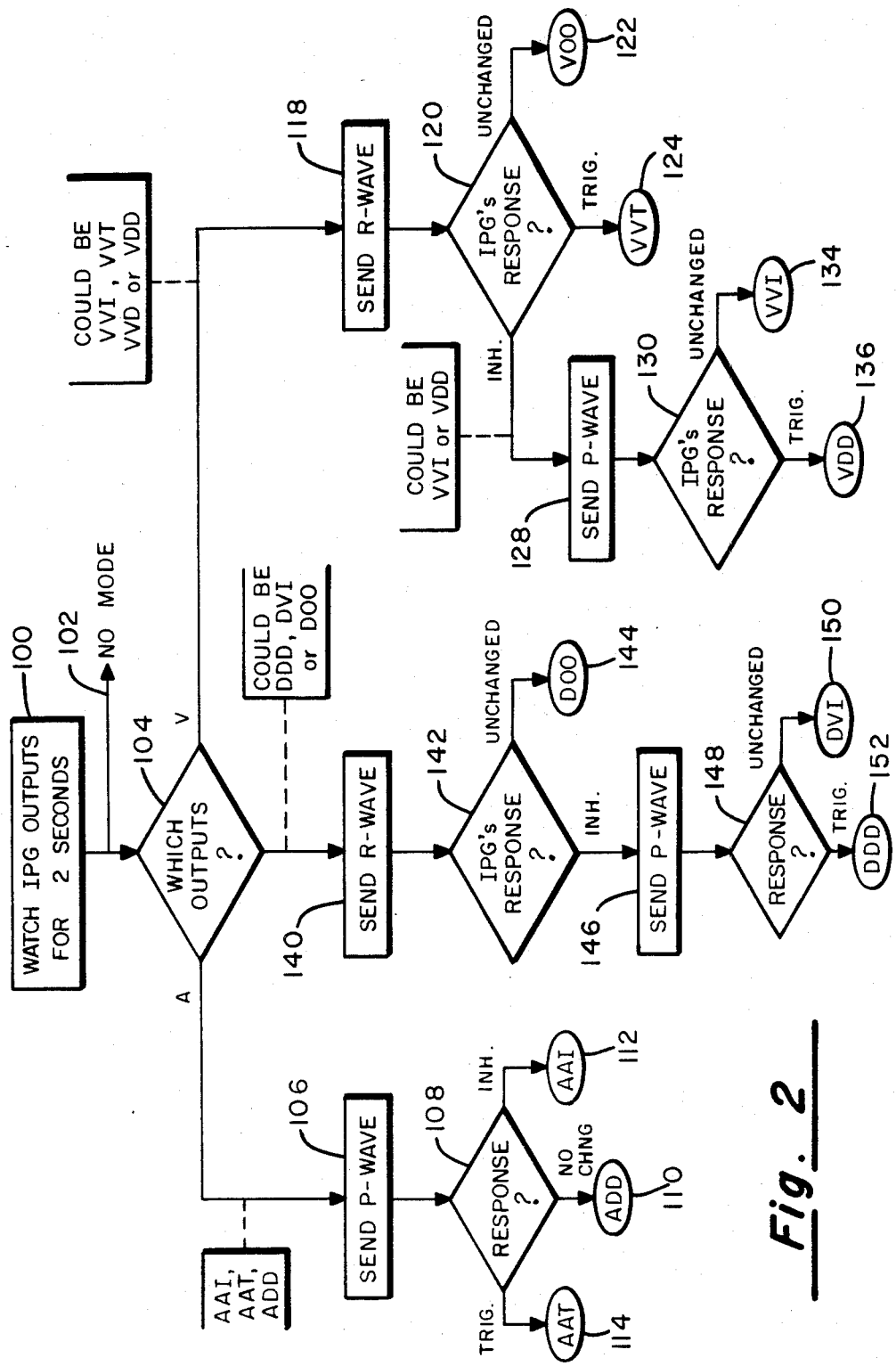
FIG. 2 is a flow chart implementation of the present invention.

A determination of the pacing modality for a pacemaker which is coupled to the pacing system analyzer 26 is conveniently implemented in software terms in the analyzer logic 32 which utilizes a conventional microprocessor. The pacing logic 22 of the pacemaker continually searches for output signals received from the atrial sense amplifier 14 and the ventricular sense amplifier 18 and coupled through the converter 28. The pacing system analyzer 26 accepts these sensed signals over a two-second period as indicated by the operation step 100 of FIG. 2. If neither an atrial or ventricular pacing output is detected during this two-second period the pacing system analyzer indicates that no mode has been programmed, as indicated by the line 102.

If only an atrial output pulse has been provided by the atrial output circuit 16, but no ventricular output pulse occurred, it is known that the pacing generator can be in one of three modes. Pacing modes are defined herein for convenience by the three-character Inter-Society Commission on Heart Disease (ICHD) code. One possible mode is the AOO mode, which is simply an atrial asynchronous pulsing mode. Another is the AAT mode, which means that pacing and sensing are occurring only in the atrial chamber and whenever a natural atrial P-wave is sensed another atrial pulse is produced after an appropriate time delay. The third possible atrial mode is the AAI mode, which means that if an atrial response, or P-wave, is sensed during a preset time period the next atrial output pulse will be inhibited which allows the heart to beat at its own natural atrial rate.

Thus, at the decision step 104, if only the atrial pulse is present, the procedure branches to the operation step 106. A operation step 106, a simulated P-wave is transmitted by the analyzer logic 32 through the converter 30 to the atrial sense amplifier just before the time the next atrial output pulse is expected. Simulated P-waves are commonly sine squared wave having a width on the order 10 milliseconds. However, in the present embodiment it is preferred to employ high amplitude pulses, to insure sensing despite the sensitivity setting of the amplifier, and having a short duration, to obtain rapid sensing. Pulses of 100 millivolts and 1 millisecond duration, for example, may be used. Upon receipt of the simulated P-wave by the atrial sense amplifier, a decision is made at the decision step 108 as to which of the three possible atrial modes the pulse generator is actually in. For example, if the pacemaker receives the simulated P-wave, and the next atrial output pulse proceeds at a fixed time from the previous one, this indicates that the simulated P-wave has not been sensed by the pacemaker and the decision is made that the pulse generator is in the AAO mode, as indicated by the result step 110.

Simulated P-wave and R-wave signals are accomplished by "calling-up" stored digital values in a memory section of the analyzer logic 32 and using these digital values to provide an analog output signal, through the digital-to-analog converter 30 to the leads 10 and 12.

On the other hand, if the pacemaker responds by not producing the next output atrial pulse when it is expected to be produced, it is known that the pacemaker is in the AAI or atrial inhibited mode, as indicated by the result step 112. A third possible mode is the atrial triggered mode, or AAT mode in which the pacemaker responds to the simulated P-wave by triggering another atrial output pulse, as indicated by the result step 114. The AAT, or atrial triggered mode, is also called the atrial synchronous mode. It is often used with adults in their working years and children, since it provides for a more natural variability of heart rate. Because proper A-V delay is maintained in this mode it allows atrial emptying before ventricular contraction, and maintains maximum pumping efficiency.

Returning to the decision step 104, it is not assumed that only a ventricular output pulse has been detected. This means that the pacing modality used could be one of four possible commonly used modes. It could be a VOO, or ventricular asynchronous mode; a VVT, or ventricular triggered mode; or VVI, or ventricular demand or inhibited mode; or VDD, or atrial synchronous mode. The VOO and VVT modes of operation are determined in a manner analagous to that employed for determination of the AOO and AAT modes. In this case a simulated R-wave, which may be the same pulse as that employed for P-wave simulation, is produced as indicated by the operation step 118 and is coupled to the ventricular sense amplifier 18 via the analyzer logic 32 and the converter 30. This signal is coupled to the amplifier at the time just before next ventricular ouptut pulse is to be produced by the ventricular output circuit 20.

If at decision step 120 the pacemaker responds to the simulated R-wave by simply ignoring the produced pulse and continues to pace at a continuous fixed rate, the pacing mode is a VOO, or asynchronous ventricular pacing mode, and this is indicated at the result step 122. If the pacemaker responds by producing a ventricular pulse shortly after the R-wave is received, the decision step 120 indicates that the VVT, or ventricular triggered, mode of operation is being employed. This mode is also called an R-triggered, or standby pacemaker mode. The R-triggering action of the pacemaker occurs when there is a natural ventricular depolarization. Since the ventricles have already been depolarized at this time, they are refractory and the production of pacer pulses at this time is disadvantageous to the extent that the average current on the battery is increased. In the event that a ventricular depolarization is not sensed, a standby R-triggered pacemaker operates in a VOO, or asynchronous mode.

VVT pacemakers are not often used, partly because of the average current drain and is primarily used in pacers where there is a high threat of external interference since the pulse will be released regardless of whether or not there is a natural ventricular depolarization.

The event that decision step 120 indicates R-wave inhibition of the pacemaker so that a subsequent ventricular pulse is not produced, there are two possible modes of operation. The pacing mode could be a VVI, or ventricular inhibited mode or a VDD, or atrial synchronous mode. In the atrial synchronous mode, there is sensing and pacing in the ventricular chamber but only sensing in the atrial chamber. A more complete definition of the VDD mode is that it is atrial synchronous, and ventricular inhibited. This means that if the atrial amplifier senses a P-wave, a ventricular output pulse will be produced after a predetermined time.

The P-wave is sent following the simulated R-wave outside of the refractory period, and a decision is made at decision step 128 based on the response of the pulse generator. If the pulse generator continues to remain inhibited as a simulated R-wave is received, followed by the simulated P-wave, a decision is made at the result step 134 that a VVI, or ventricular inhibited, mode of operation is employed. If the pulse generator under consideration was first inhibited by the simulated R-wave of step 118, and the subsequent simulated P-wave of step 128 causes a ventricular output pulse, then it is determined at decision step 130 that the pulse generator is in the VDD or atrial synchronous mode.

In the event that both atrial and ventricular pacing pulses are sensed, the operation moves to operation step 140 which results in a simulated R-wave being sent to the pacer before the next ventricular pacing pulse is generated. Entry of the routine to the decision step 140 indicates that three possible pacing modes exist. These are the DVI or A-V sequential mode, in which there is sensing and pacing in the V or ventricular chamber, but only pacing in the A or atrial chamber; the fully automatic, or DDD, mode, in which there is pacing and sensing in both chambers; and the DOO mode, in which asynchronous pulses are applied sequentially in the atrial and ventricular chambers.

After transmission of a simulated R-wave to the cardiac pulse generator pacemaker the response of the pacemaker is determined at decision step 142 so that if pacing continues at an asynchronous rate after the R-wave is sent decision step 142 indicates that the pulse generator is in a DOO mode at the result step 144. Since both the DDD and DVI modes of operation result in ventricular output inhibition upon receipt of R-waves by the ventricular sense amplifier, once inhibition has been determined, at step 142 a simulated P-wave will be transmitted to the atrial output circuit at step 146. In step 148 the response of the pacemaker to the simulated P-wave is determined.

If the pulse generator continues to operate unaffected by the P-wave, it is known that the pulse generator is in a DVI mode which is indicated at result step 150, since such a mode does not use the atrial sensing circuit. In other words, the DVI mode operates very similar to the VVI except that the atrial chamber is paced just prior to the ventricular pacing pulse, but both modes inhibited if the R-wave is sensed before the end of the A-V or atrial-ventricular, interval. If the pacemaker responds to receipt of the P-wave of step 146 by producing a ventricular trigger output, the decision step 148 indicates the pulse generator is in the DDD mode at result step 152.

What is claimed is:

1. A pacing system analyzer for determining the mode of an implantable cardiac pacemaker comprising means coupled to said cardiac pacer for sensing when an atrial pacing pulse has been emitted, means for transmitting a simulated atrial P-wave signal to said cardiac pacer, response determining means for indicating the cardiac pacer as in an AOO mode if no change occurs, for indicating that it is in an AAI mode if said cardiac pacer is inhibited producing further atrial pulses and for indicating that said pacer is in an AAT mode if said simulated P-wave causes the triggering of an additional atrial output pulse.

2. A pacing system analyzer for determining the mode of an implantable cardiac pacer comprising means coupled to said pacer for determining when a ventricular pulse is emitted by said pacer, first transmission means for transmitting a simulated ventricle R-wave to said pacer. First response determining means for determining the response of said pacer to said simulated R-wave and for indicating that the pacer is in a VOO mode if there is no change in response to said R-wave, for indicating that the pacer is in a VVT mode if the pacer responds by emitting further ventricular pacing pulse and for transmitting a simulated atrial P-wave to said pacer if said first response means determines that said pacer is in a ventricular inhibited mode in which the ventricular output pulse is inhibited in response to said simulated R-wave, second response means responsive to the transmission of said simulated P-wave which determines that said caridac pacer is in a VVI mode if the cardiac pacer does not change its ventricle pulsing rate in response to said P-wave and which determines that the pacer is in a VDD mode if the second response means determines that a ventricular pacing pulse has been triggered by response to said simulated P-wave.

3. The pacing system analyzer for analyzing the pacing mode of a cardiac pacer comprising means for sensing the generation of both atrial and ventricular pacing pulses by said cardiac pacer, means for sensing a simulated R-wave to said cardiac pacer when both said atrial and ventricle pulses have been detected, first response means for determining the response of said cardiac pacer to said simulated R-wave for determining that the pacer is in a DOO mode when said pacer does not change its atrial and ventricular pacing rates in response to said R-wave and for determining when said cardiac pacer is inhibited in response to said simulated R-wave, means for transmitting a simulated P-wave to said cardiac pacer if said cardiac pacer is inhibited by said R-wave transmission and second response means for determining the response of said cardiac pacer to said P-wave and for determining that the pacer is in a DVI mode if the cardiac pacer does not change its response and continues to emit atrial pacing pulses after the simulated P-wave is sent to it and for determining that the pacer is in a DDD mode if the cardiac pacer responds to the simulated P-wave by emitting a ventricular triggered pacing pulse in response thereto.

* * * * *

UNITED STATES PATENT AND TRADEMARK OFFICE
CERTIFICATE OF CORRECTION

PATENT NO. : 4,503,858

DATED : 12 March 1985

INVENTOR(S) : Markowitz et al.

It is certified that error appears in the above-identified patent and that said Letters Patent are hereby corrected as shown below:

Column 3,
  Line 3, "not" should be --now--.

Signed and Sealed this

Fourth Day of February 1986

[SEAL]

Attest:

DONALD J. QUIGG

Attesting Officer

Commissioner of Patents and Trademarks